US006939440B2

(12) United States Patent
Drew et al.

(10) Patent No.: US 6,939,440 B2
(45) Date of Patent: Sep. 6, 2005

(54) CREPED AND IMPRINTED WEB

(75) Inventors: Robert A. Drew, Dunwoody, GA (US); Frank G. Druecke, Oshkosh, WI (US); Patricia Riedl, London (GB); Peter J. Allen, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 31 days.

(21) Appl. No.: 10/323,709

(22) Filed: Dec. 18, 2002

(65) Prior Publication Data

US 2003/0201081 A1 Oct. 30, 2003

Related U.S. Application Data

(60) Division of application No. 10/013,337, filed on Dec. 10, 2001, now Pat. No. 6,547,926, which is a continuation-in-part of application No. 09/854,145, filed on May 11, 2001, now Pat. No. 6,585,855.
(60) Provisional application No. 60/204,083, filed on May 12, 2000.

(51) Int. Cl.[7] ............................. B31F 1/12; D21H 27/30
(52) U.S. Cl. ...................... 162/113; 162/109; 162/117; 162/123; 428/153
(58) Field of Search ........................ 162/109, 111–113, 162/117, 123, 204–207; 428/152–153

(56) References Cited

U.S. PATENT DOCUMENTS

| | | | |
|---|---|---|---|
| 1,643,147 A | 9/1927 | Angier | |
| 2,934,865 A | 5/1960 | Pfeiffer | |
| 2,947,058 A | 8/1960 | Landells et al. | |
| 3,207,657 A | 9/1965 | Wagner et al. | |
| 3,230,136 A | 1/1966 | Krake | |
| 3,290,209 A | 12/1966 | Ihrman | |
| 3,382,552 A | 5/1968 | Davis et al. | |
| 3,523,865 A | 8/1970 | Ihrman | |
| 3,866,277 A | 2/1975 | Hojyo | |
| 3,879,257 A | 4/1975 | Gentile et al. | |
| 3,903,342 A | 9/1975 | Roberts, Jr. | |
| 3,906,853 A | 9/1975 | Wohlfarter | |
| 3,994,771 A | 11/1976 | Morgan, Jr. et al. | |
| 4,166,001 A | 8/1979 | Dunning et al. | |
| 4,225,382 A | 9/1980 | Kearney et al. | |
| 4,300,981 A | 11/1981 | Carstens | |
| 4,309,246 A | 1/1982 | Hulit | |
| 4,344,818 A | 8/1982 | Nuttall et al. | |
| 4,356,059 A * | 10/1982 | Hostetler .................... | 162/111 |
| 4,529,480 A | 7/1985 | Trokhan | |
| 4,551,199 A * | 11/1985 | Weldon ...................... | 162/109 |
| 4,637,859 A | 1/1987 | Trokhan | |
| 4,689,119 A * | 8/1987 | Weldon ...................... | 162/281 |
| 5,087,324 A | 2/1992 | Awofeso et al. | |
| 5,102,501 A | 4/1992 | Eber et al. | |
| 5,129,988 A | 7/1992 | Farrington, Jr. | |
| 5,147,505 A | 9/1992 | Altman | |
| 5,230,776 A | 7/1993 | Andersson et al. | |
| 5,494,554 A | 2/1996 | Edwards et al. | |
| 5,529,665 A | 6/1996 | Kaun | |
| 5,562,805 A | 10/1996 | Kamps et al. | |
| 5,656,132 A | 8/1997 | Farrington, Jr. et al. | |
| 5,667,636 A * | 9/1997 | Engel et al. ................ | 162/117 |
| 5,672,248 A | 9/1997 | Wendt et al. | |
| 5,695,607 A | 12/1997 | Oriaran et al. | |
| 5,746,887 A * | 5/1998 | Wendt et al. ............... | 162/109 |
| 5,759,346 A | 6/1998 | Vinson | |
| 5,772,845 A * | 6/1998 | Farrington et al. ......... | 162/109 |
| 5,840,787 A | 11/1998 | West et al. | |
| 5,851,353 A * | 12/1998 | Fiscus et al. ............... | 162/113 |
| 5,851,629 A | 12/1998 | Oriaran et al. | |
| 5,882,479 A | 3/1999 | Oriaran et al. | |
| 5,932,068 A | 8/1999 | Farrington, Jr. et al. | |
| 5,958,185 A | 9/1999 | Vinson et al. | |
| 6,017,418 A | 1/2000 | Oriaran et al. | |
| 6,033,523 A | 3/2000 | Dwiggins et al. | |
| 6,033,761 A | 3/2000 | Dwiggins et al. | |
| 6,051,104 A | 4/2000 | Oriaran et al. | |
| 6,068,731 A | 5/2000 | Dwiggins et al. | |
| 6,096,169 A | 8/2000 | Hermans et al. | |
| 6,103,063 A | 8/2000 | Oriaran et al. | |
| 6,113,740 A | 9/2000 | Oriaran et al. | |
| 6,120,642 A | 9/2000 | Lindsay et al. | |
| 6,143,131 A | 11/2000 | Dwiggins et al. | |
| 6,143,135 A | 11/2000 | Hada et al. | |
| 6,149,767 A * | 11/2000 | Hermans et al. ........... | 162/109 |
| 6,153,053 A | 11/2000 | Harper et al. | |
| 6,197,154 B1 | 3/2001 | Chen et al. | |

(Continued)

FOREIGN PATENT DOCUMENTS

| | | |
|---|---|---|
| CA | 2241820 | 2/1999 |
| EP | 0613979 B1 | 7/1994 |
| EP | 0539703 B1 | 5/1997 |
| EP | 0618329 B1 | 8/1999 |
| EP | 0675225 B1 | 2/2000 |
| GB | 2098637 A | 11/1982 |
| WO | WO9513424 | 5/1995 |
| WO | WO00082531 | 2/2000 |
| WO | WO0185438 A2 | 11/2001 |
| WO | WO0185438 A3 | 11/2001 |

Primary Examiner—José A. Fortuna
(74) Attorney, Agent, or Firm—Dority & Manning, P.A.

(57) ABSTRACT

Paper products, such as wiping products, are disclosed that have a fabric-imprinted pattern in combination with a crepe pattern. In producing paper products according to the invention, a base web containing pulp fibers is formed. Once the base web is substantially dry, the web is creped to form a first pattern. The creped web is then placed between two moving conveyors and guided around one or more compression inducing elements. As the web is guided around the compression inducing element in between the two conveyors, shear forces and compressive forces are imparted to the web that form a fabric-imprinted pattern superimposed on the crepe pattern. In one embodiment, the fabric-imprinted pattern comprises high density troughs.

22 Claims, 7 Drawing Sheets

U.S. PATENT DOCUMENTS

| | | |
|---|---|---|
| 6,210,528 B1 | 4/2001 | Wolkowicz |
| 6,228,220 B1 * | 5/2001 | Hada et al. .................. 162/203 |
| 6,287,426 B1 | 9/2001 | Edwards et al. |
| 6,361,651 B1 | 3/2002 | Sun |
| 6,547,926 B2 * | 4/2003 | Drew et al. .................. 162/113 |
| 6,607,635 B2 | 8/2003 | Bakken et al. |
| 6,620,865 B2 | 9/2003 | Westland et al. |
| 6,630,054 B1 | 10/2003 | Graef et al. |
| 2002/0166646 A1 * | 11/2002 | Drew et al. .................. 162/111 |
| 2003/0201081 A1 * | 10/2003 | Drew et al. .................. 162/111 |
| 2003/0201083 A1 | 10/2003 | Marsh |
| 2003/0203195 A1 | 10/2003 | Marsh |
| 2003/0213574 A1 | 11/2003 | Bakken et al. |

* cited by examiner

CREPED AND IMPRINTED WEB

CROSS REFERENCE TO RELATED APPLICATIONS

This application is a divisional application claiming priority to U.S. application Ser. No. 10/013,337 entitled "PROCESS FOR INCREASING THE SOFTNESS OF BASE WEBS AND PRODUCTS MADE THEREFROM", filed Dec. 10, 2001, now U.S. Pat. No. 6,547,926, which is a Continuation-in-part of Utility Application filed on May 11, 2001 having U.S. application Ser. No. 09/854,145, now U.S. Pat. No. 6,585,855, which was based on a Provisional Application filed on May 12, 2000 having U.S. Application No. 60/204,083.

BACKGROUND OF THE INVENTION

Products made from base webs such as bath tissues, facial tissues, paper towels, industrial wipers, foodservice wipers, napkins, medical pads, and other similar products are designed to include several important properties. For example, the products should have a soft feel and, for most applications, should be highly absorbent. The products should also have good stretch characteristics and should resist tearing. Further, the products should also have good strength characteristics, should be abrasion resistant, and should not deteriorate in the environment in which they are used.

In the past, many attempts have been made to enhance and increase certain physical properties of such products. Unfortunately, however, when steps are taken to increase one property of these products, other characteristics of the products may be adversely affected. For instance, the softness of nonwoven products, such as various paper products, can be increased by several different methods, such as by selecting a particular fiber type, by calendering, or by reducing cellulosic fiber bonding within the product. Increasing softness according to one of the above methods, however, may adversely affect the strength of the product. Conversely, steps normally taken to increase the strength of a fibrous web typically have an adverse impact upon the softness, the stiffness, or the absorbency of the web.

The present invention is directed to improvements in base webs and to improvements in processes for making the webs in a manner that optimizes the physical properties of the webs. In particular, the present invention is directed to a process for improving the tactile properties, such as softness and stiffness, of base webs without severely diminishing the strength of the webs.

SUMMARY OF THE INVENTION

In general, the present invention is directed to a creped web product having a unique fabric-imprinted pattern and a process for producing the product. The process of the present invention includes forming a base web, creping the base web in a manner known in the art, and then forming a unique, fabric imprinted pattern on at least one surface of the web at the same time as softening the web through a shear-inducing process.

To form the fabric imprinted pattern on the surface of the base web, the creped web is first placed between two moving conveyors. The conveyor/web sandwich thus produced is then guided around one or more compression inducing elements. As the conveyors are guided around the element (s), both shear forces and compressive forces are imparted to the web. The compressive forces can be such that a fabric imprinted pattern is formed on the surface of the base web while the shear forces can soften the web.

The compressive forces acting on the web can be greatest at those areas where the fabric knuckles of the conveyor contact the surface of the web. This can cause the fabric imprinted pattern formed on the web surface to be a series of high density troughs superimposed on the previously formed crepe pattern of the web. In an alternative embodiment, a fabric imprinted pattern can be formed on both surfaces of the web.

The compression inducing element can be any suitable element which can impart the necessary shear and compressive forces to the web. For instance, in one embodiment, the compression inducing element can comprise a roll having a small effective diameter of less than about ten inches. Particularly, the compression inducing element can have an effective diameter of less than about seven inches. More particularly, the compression inducing element can have and effective diameter of from about 2 to about 5 inches.

The web can be essentially dry when guided around the compression inducing element of the present invention. For example, the web can have a moisture content of less than about 10% by weight.

In order to suitably soften and form the pattern in the web, the conveyors should be under a tension when wrapped around the shear/compression inducing element. For example, the conveyors can be wrapped around the element at least 30°. More specifically, the conveyors can be wrapped around the element at least 50°. The conveyors can be under a tension of at least 5 pounds per linear inch when guided around the compression inducing element.

The unique creped web product of the present invention can be formed of any suitable base web. For example, the base web can have a basis weight between about 5 and about 40 grams per square meter. The paper product can be a single-ply product or a multi-ply product. Additionally, any single ply of the paper product can be a homogeneous or a stratified web. The creped paper product of the present invention can be formed of any suitable fiber type.

The paper product of the present invention is a soft, strong creped product which can exhibit limited caliper decrease during processing. For example, the paper product of the present invention can exhibit a geometric mean tensile strength of greater than about 200 grams per inch. More specifically, the paper product can exhibit a geometric mean tensile strength of greater than about 250 g/in.

The bulk of the creped web product can be greater than that of other calendered tissue products. For example, the bulk can be greater than about 7.5 cc/gram. More specifically, the bulk can be greater than about 8.5 cc/gram.

Likewise, the caliper of the disclosed paper product can be greater than that of a similar calendered, creped web product. In one embodiment, the caliper can be greater than about 250 microns. More specifically, the caliper can be greater than about 275 microns.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Repeat use of reference characters in the present specification and drawings is intended to represent same or analogous features or elements of the present invention.

DETAILED DESCRIPTION OF PREFERRED EMBODIMENT

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to a process for improving the tactile properties of base webs without a subsequent substantial loss in tensile strength. The present invention is also directed to webs made from the process. In particular, the process of the present invention is well suited to increasing the softness and decreasing the stiffness of base webs, such as webs containing pulp fibers. Further, in some applications, such as when producing a wet-pressed, creped product, the present invention can provide a soft, bulky tissue product without the necessity of subsequent softening processes. For example, the creped tissue product of the present invention can be a suitably soft product without an additional calendering process. As a result, the paper product can have increased caliper and bulk over similar calendered products. Additionally, the creped tissue product of the present invention can have a unique, fabric-imprinted pattern superimposed on at least one surface of the web.

Generally speaking, the process of the present invention includes the step of subjecting a previously formed base web to a shearing force in an amount sufficient to improve the softness of the web. For instance, a previously creped base web can be subjected to a shearing force in an amount sufficient to improve softness such that a subsequent calendering process is not required to obtain a soft, strong tissue.

In accordance with the present invention, a shearing force can be applied to the web by placing the web between a pair of moving conveyors. As used herein, a conveyor is intended to refer to a flexible sheet, such as a wire, a fabric, a felt, and the like. Once the base web is placed in between the moving conveyors, a speed differential is created between the two conveyors. This speed differential can impart a shearing force to the web. For example, in one embodiment, the conveyors can be guided around at least one shear-inducing element, such as a roll, while the web is sandwiched between the two conveyors. The shear-inducing element can rotate or can be stationary and typically has a small effective diameter, such as less than about 10 inches.

The moving conveyors have a sufficient amount of wrap around the shear-inducing element and are placed under sufficient tension to create shear forces that act upon the base web. Specifically, passing the conveyors over the shear-inducing element causes a speed differential in the conveyors which creates a shearing force that breaks bonds within the web or otherwise disrupts fiber entanglement within the web where the web is weakest. Through this process, the softness of the web increases while the stiffness of the web is reduced. Unexpectedly, the present inventors have discovered that this softening occurs with substantially less loss of tensile strength than would be expected at the softness levels obtained.

In addition to inducing shearing forces on the web, the process can also induce compressive forces that act on the web. As the conveyors pass over the shear-inducing element, not only shearing forces can be imparted in a direction tangential to the surface of the web, but also compressive forces can be imparted in a direction perpendicular to the surface of the web. Thus the shear-inducing element may also be referred to as a compression inducing element.

Base webs that may be used in the process of the present invention can vary depending upon the particular application. In general, any suitable base web may be used in the process in order to improve the tactile properties of the web. Further, the webs can be made from any suitable type of fiber.

For example, the manner in which the base web of the present invention is formed may vary depending upon the particular application. In one embodiment, the web can contain pulp fibers and can be formed in a wet-lay process according to conventional paper making techniques. In a wet-lay process, the fiber furnish is combined with water to form an aqueous suspension. The aqueous suspension is spread onto a wire or felt and dried to form the web.

Figure 2:
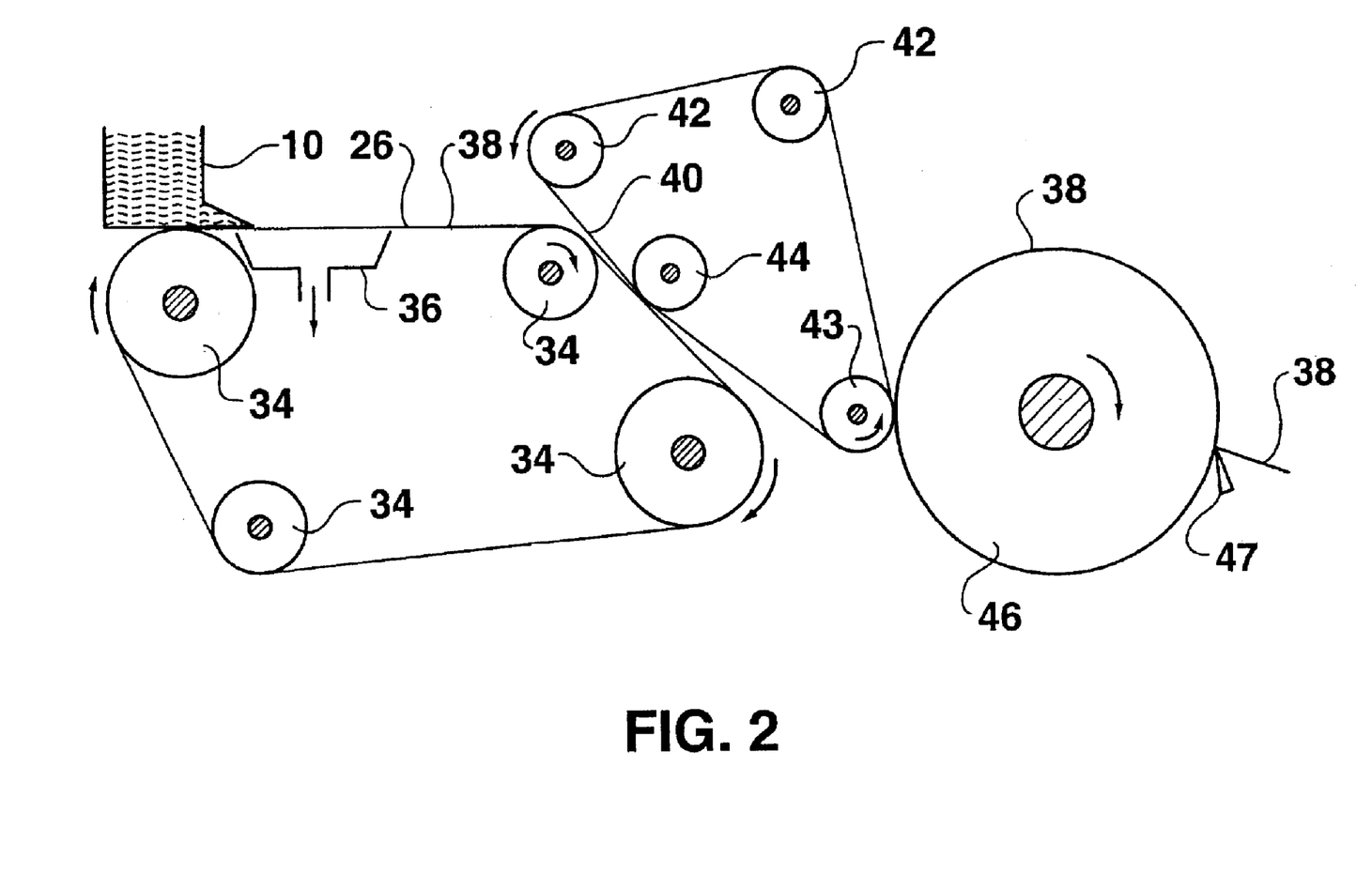
FIG. 2 is a schematic diagram of a fibrous web forming machine that crepes one side of the web.

Referring to FIG. 2, one embodiment of a process for producing a base web that may be used in accordance with the present invention is illustrated. The process illustrated in the figure depicts a wet-lay process, although, as described above, other techniques for forming the base web of the present invention may be used.

As shown in FIG. 2, the web-forming system includes a headbox 10 for receiving an aqueous suspension of fibers. Headbox 10 spreads the aqueous suspension of fibers onto a forming fabric 26 that is supported and driven by a plurality of guide rolls 34. A vacuum box 36 is disposed beneath forming fabric 26 and is adapted to remove water from the fiber furnish to assist in forming a web.

From forming fabric 26, a formed web 38 is transferred to a second fabric 40, which may be either a wire or a felt. Fabric 40 is supported for movement around a continuous path by a plurality of guide rolls 42. Also included is a pick up roll 44 designed to facilitate transfer of web 38 from fabric 26 to fabric 40. The speed at which fabric 40 can be driven is approximately the same speed at which fabric 26 is driven so that movement of web 38 through the system is consistent. Alternatively, the two fabrics can be run at different speeds, such as in a rush transfer process, in order to increase the bulk of the webs or for some other purpose.

From fabric 40, web 38, in this embodiment, is pressed onto the surface of a rotatable heated dryer drum 46, such as a Yankee dryer, by a press roll 43. Web 38 is lightly pressed into engagement with the surface of dryer drum 46 to which it adheres, due to its moisture content and its preference for the smoother of the two surfaces. As web 38 is carried through a portion of the rotational path of the dryer surface, heat is imparted to the web causing most of the moisture contained within the web to be evaporated.

Web 38 is then removed from dryer drum 46 by a creping blade 47. Creping web 38 as it is formed reduces internal bonding within the web and increases softness. Creping can also cause the surfaces of the web to take on a conventional crepe structure having a recognizable crepe pattern.

Figure 7:
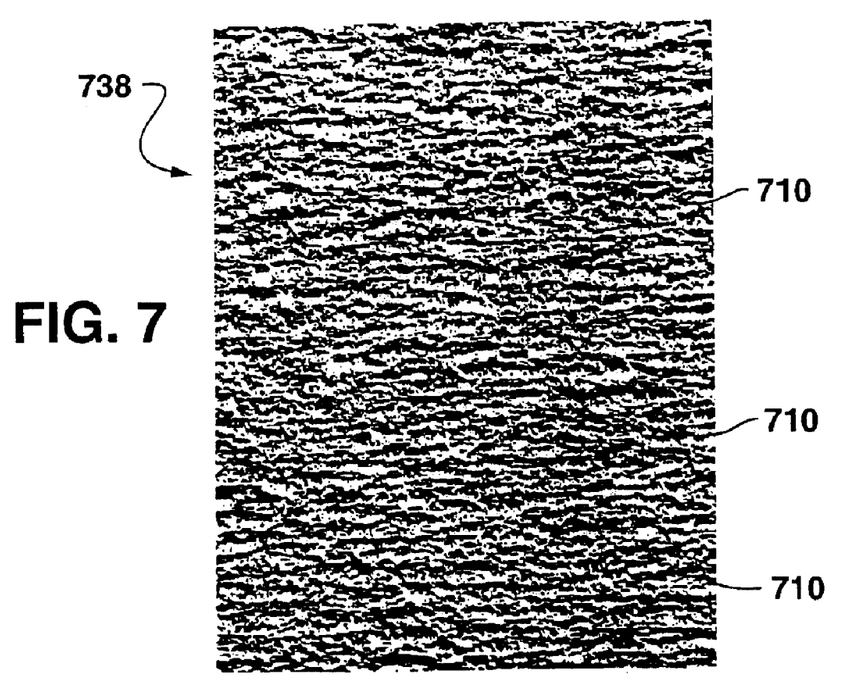
FIG. 7 is an illustration of the surface features of a typical commercial facial tissue which has been creped.

FIG. 7 illustrates the typical crepe pattern formed on the surface of a web 738. The crepe pattern of a web 738 which has been subjected to a creping process can include an undulatory pattern including crepe peaks 710 or folds on the surface of the base web 738. The crepe pattern is generally visible on both sides of the web, though it can be more clearly discerned on the side of the web which contacts the creping blade. In general, the frequency and height of the crepe peaks 710 forming the crepe pattern can vary depending on various factors including, for example, line speed and web tension. In general the crepe pattern can include approximately 1 to 4 crepe peaks per millimeter in the machine direction.

Figure 3:
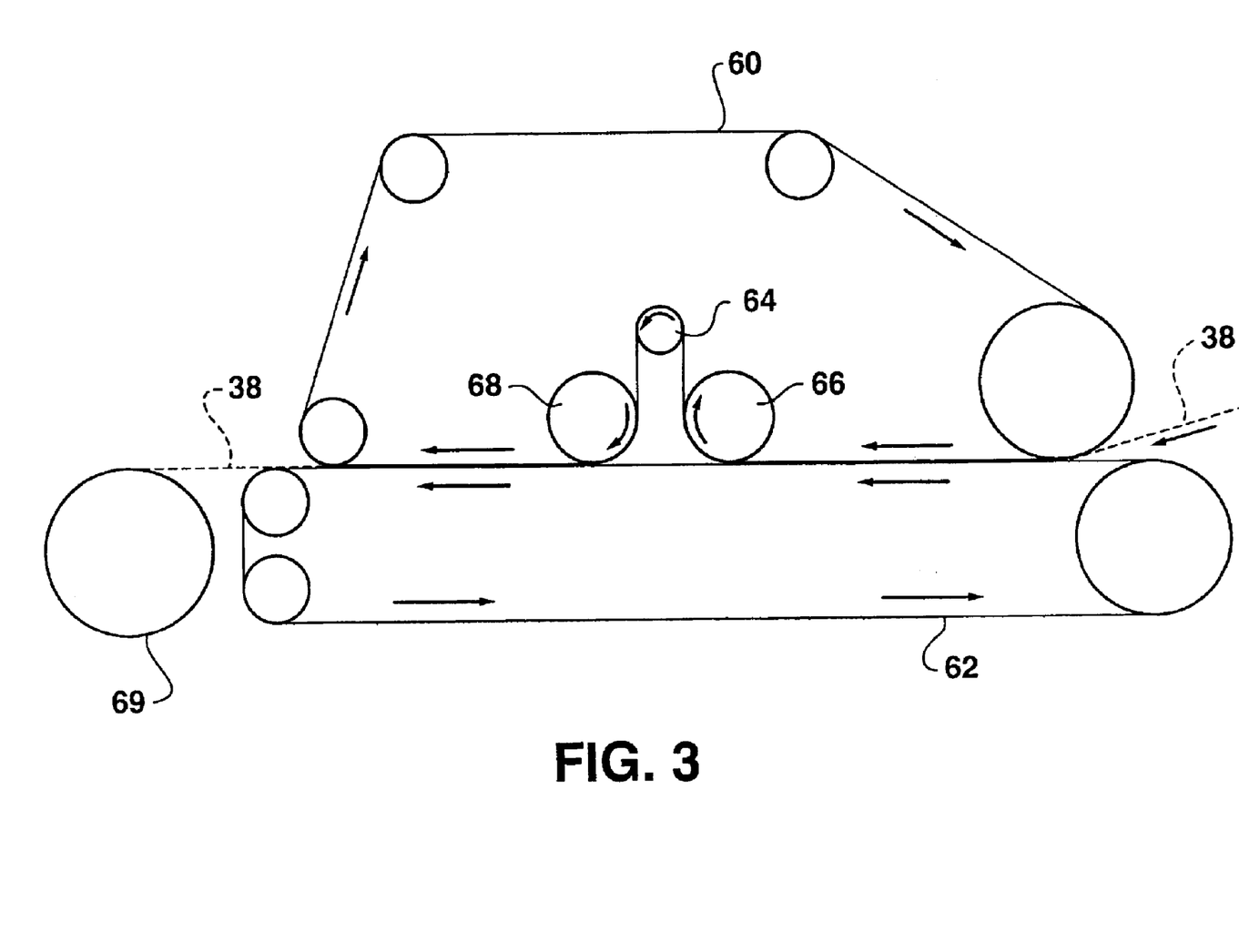
FIG. 3 is a schematic diagram of one embodiment for a process for improving the tactile properties of a formed base web in accordance with the present invention.

After the base web 38 is formed, such as through the process illustrated in FIG. 2, or any other suitable process, the web is placed between a pair of moving conveyors and pressed around a shear-inducing element in accordance with the present invention. For instance, one embodiment of a process for improving the tactile properties of a base web in accordance with the present invention is illustrated in FIG. 3. As shown, the base web 38 is supplied between a first moving conveyor 60 and a second moving conveyor 62. The speed at which the conveyors 60 and 62 are moving is generally not critical to the present invention. For most commercial applications, the conveyors can be moving at a speed of from about 1,000 feet per minute to about 6,000 feet per minute.

Once positioned in between the first conveyor 60 and the second conveyor 62, the base web and the conveyors are guided around a shear-inducing roll 64 by a pair of support rolls 66 and 68. In accordance with the present invention, the conveyors 60 and 62 are placed under tension and are wrapped around the shear-inducing roll 64 in amounts sufficient to create shear forces that act upon the base web 38. In particular, when the conveyors are passed over the shear-inducing roll, a speed differential develops in the conveyors. Due to the interaction between the surfaces of the conveyors and the contacting surface of the web, the speed differential of the conveyors can be translated into a speed differential between the two web surfaces. Factors which can affect the web surface/conveyor surface interaction can include but are not limited to, for example, the coefficient of friction at the conveyor surfaces, the tension of the conveyors, and the moisture content of the web. A speed differential between the two web surfaces can create shearing forces which act upon the base web. The shearing forces can break bonds within the web where the web is weakest, which subsequently increases the softness and decreases the stiffness of the web.

Further, the present inventors have discovered that these improvements are realized without a significant decrease in tensile strength as normally occurs in other processes designed to increase softness.

The inventors have also unexpectedly discovered that the process of the present invention can produce a web with distinct properties. Specifically, the web produced by the present invention can show improved characteristics in terms of both aesthetic properties as well as physical properties. For example, it has been discovered that the process of the present invention can provide a unique patterned structure to a creped base web while maintaining suitable strength and softness and actually increasing tissue bulk over other creped and calendered products.

In general, a conventionally produced tissue product can be wet-pressed onto a heated dryer and then removed from the drum by a creping blade. As the web is creped from the dryer drum, internal bonding within the web is reduced and softness is increased. The creped web can also take on a conventionally known crepe pattern on the surface of the web. FIG. 7 illustrates the fine crepe structure of a typical creped tissue 738. As can be seen, the surface of the creped tissue can include an undulatory pattern of approximately 1 to 4 crepe peaks 710 or folds per millimeter. This typical crepe structure results from the deformation of the fiber matrix during impact with a blade while the web is creped from the drum of the heated dryer.

In the past, subsequent to a creping process, a web was calendered in order to increase product softness and smoothness. For example, a web could be calendered in a steel on steel calendaring configuration at high PLI loading to impart a softer, smoother feel to the web. One undesirable result of the calendering process, however, was a relatively large decrease in caliper of the tissue product.

In accordance with the present invention, it has been discovered that a wet-pressed, creped web, such as that illustrated in FIG. 7, can be fed between two moving conveyors and guided around one or more shear inducing rolls. The shear forces imparted to the web through the process of the present invention can provide a soft, strong tissue product without the need of a subsequent calendering process.

As the web is guided around a shear inducing roll, not only shear forces, but also compressive forces are imparted on the web. Thus the shear-inducing roll can equally be referred to as a compression inducing roll.

The nature of the compressive forces imparted to the web through the process of the present invention can impart unique characteristics to the creped web. For example, the forces imparted on the web through the process of the present invention can soften the web while limiting the amount of total caliper reduction of the soft tissue. Additionally, the compressive forces of the present invention can provide a unique, visible pattern to a creped web.

As previously discussed, at some point subsequent to the creping process, the tissue product of the present invention can be fed between a pair of moving conveyors. The conveyors can be formed of any suitable paper making fabric, such as, for example, a wire, a fabric, a felt, or the like. Additionally, the conveyors can be of different construction from each other. For instance, one or both of the conveyors can be a highly textured forming fabric or other substrate including a three dimensional structure in which the fabric knuckles can extend above the major plane of the fabric body. Such three dimensional fabrics include, for instance, those disclosed in commonly owned U.S. patent application Ser. No. 08/912,906, "Web Resilient Webs and Disposable Articles Made therewith" file Aug. 15, 1997 by Chen, et al.; U.S. Pat. No. 5,672,248 to Wendt, et al.; U.S. Pat. No. 5,656,132 to Farrington, et al.; U.S. Pat. No. 6,120,642 to Lindsay and Burazin; U.S. Pat. No. 6,096,169 to Hermans, et al.; U.S. Pat. No. 6,197,154 to Chen, et al.;

U.S. Pat. No. 6,143,135 to Hada, et al. and commonly owned U.S. patent application Ser. No. 09/166,863 to Burazin, et al. all of which are herein incorporated by reference to their entireties.

Any suitable forming fabric can be used in the process of the present invention. For example, in one embodiment, the top and bottom forming fabrics can be similar fabrics and have a mesh count of about 30 by 36 and an open area of about 25.8%. One example of such a fabric is fabric style number 937 supplied by the AstenJohnson Corporation.

In one embodiment of the present invention, as the web and outer fabrics are fed around the shear inducing roll, compressive forces can be transmitted to the web. The compressive forces can be such, however, that the force is not equally distributed to the nonwoven web. For example, the compressive forces can increase across the web at those points corresponding to the fabric knuckles, with the greatest compressive forces occurring where the fabric knuckles extend above the fabric plane by the greatest amount, and the lowest compressive forces occurring at the lowest point of the fabric plane.

The sum of the forces acting on the web at the shear/compression inducing element can impart several unique benefits to a creped product. For example, the shear forces can provide a softer web product. Additionally, the compressive forces can impart a unique fabric-imprinted pattern on at least one surface of the web. Also, the total caliper reduction of the web due to the compressive forces can be much less than that experienced by base webs subjected to a traditional calendering process. As such, webs made according to the present invention can have a greater bulk than many comparative conventional products.

Figure 8:
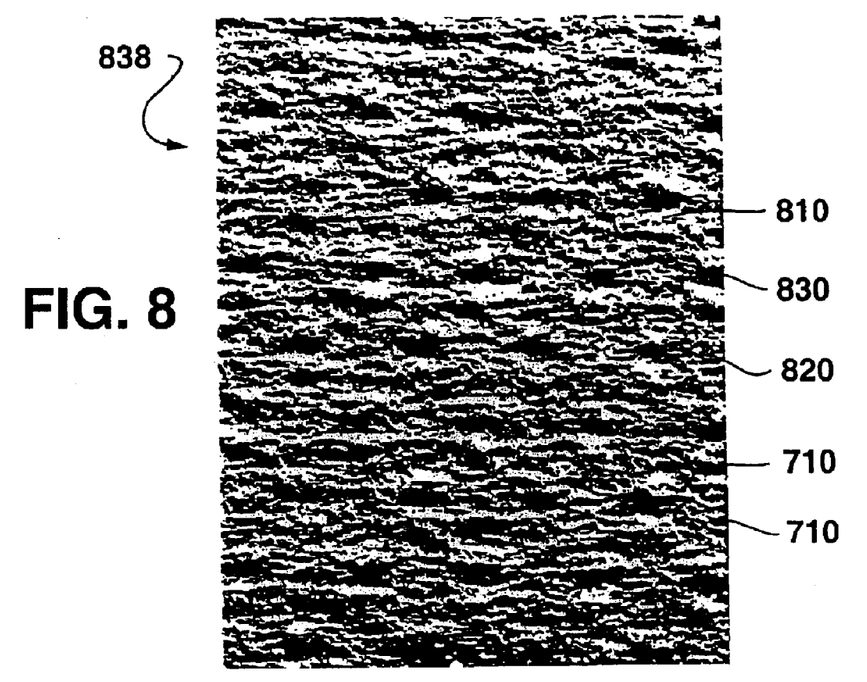
FIG. 8 is an illustration of the surface features of a tissue which has been creped followed by processing according to the present invention.

FIG. 8 illustrates a wet-pressed, creped nonwoven web 838 which has been subjected to the process of the present invention. As can be seen, the web includes not only the crepe fold structure 710 typical of a conventional creped product, similar to the base web illustrated in FIG. 7, but also includes a superimposed undulatory pattern which has been imprinted on the surface of the tissue made up of a series of larger troughs 810, 820, 830. In general, the location of the troughs can correspond to the high knuckle areas of the forming fabric abutting the web as it travels around the shear inducing roll(s). The compressive forces acting on the web at the fabric knuckles can cause the web fiber density to increase in proportion to the increasing height of the fabric knuckles, with the highest fiber density occurring in the center of a trough 810, corresponding to the maximum height of the corresponding fabric knuckle. In other words, a single trough 810 in the product web can have a density gradient across the trough, with the greatest fiber density occurring at the depth, or center of the trough, and fiber density decreasing outwardly toward the higher plane of the web. The fabric-imprinted pattern thus produced can be visible on one or both sides of the web, depending on the total amount of compressive forces acting on the web.

In the web 838 illustrated in FIG. 8, the fabric-imprinted pattern can include high density troughs 810, 820, and 830. As can be seen, troughs 810 and 820 are aligned in the machine direction and troughs 810 and 830, or alternatively troughs 820 and 830, are aligned in the diagonal direction of the web. Troughs 810 and 820, aligned in the machine direction, can be separated by a distance of between about 3 and about 4 millimeters. More specifically, high density troughs 810 and 820 can be aligned in the machine direction of the web and separated by a distance of about 3.6 millimeters. Trough 810 and trough 830, or alternatively trough 820 and 830 can be aligned in a diagonal direction in the fabric imprinted pattern and can be separated by between about 2 and about 3 millimeters. More specifically, high density troughs located on the diagonal of the fabric imprinted pattern, such as troughs 810 and 830, can be separated by about 2.3 millimeters.

The pattern imparted on to the web, such as that illustrated in FIG. 8, can be any desired pattern, and can be controlled through formation and selection of the forming fabrics used in the process. For example, a pattern can be impressed upon only one side of the web when only one of the sandwiching fabrics includes suitably high knuckles and the second forming fabric is a relatively smooth fabric. Alternatively, both of the forming fabrics can be formed of high knuckle woven fabrics, in which case both sides of the base web can have fabric-imprinted patterns of high density troughs on the surfaces. The overall form of the pattern can be merely the repetition of a regular weaving pattern used on the forming fabric, as is shown in FIG. 8, or, alternatively, the forming fabric can be formed such that the high knuckles form recognizable shapes. In such an embodiment the high density troughs, when viewed together, can form shapes, letters, or some other desired pattern. Additionally, a pattern can be chosen to impart lines of additional strength on the tissue product.

In addition to forming a visible pattern on one or both surfaces of the web, the localized compressive forces of the present process can limit the total amount of caliper reduction of the softened web when compared to other softening processes used in the past. For example, the shear inducing process of the present invention can produce a unique soft web in which other softening processes, such as for example, calendering processes, are no longer required.

Additionally, the compressive forces acting on the web, while large enough at the fabric knuckles to imprint the unique pattern, can be less over the entire surface of the web than is found in calendering processes. As a result, the web of the present invention can exhibit a limited reduction in overall caliper, which can be less than that found in a similar base web which has been calendered. For example, the shear inducing process of the present invention can produce a soft, creped tissue product, and yet reduce the caliper of the tissue sheet by less than about 20%. More particularly, the shear inducing process of the present invention can reduce the caliper of a wet-pressed, creped tissue sheet by less than about 10%.

In light of the limited amount of caliper reduction attained in producing the soft tissue product of the present invention, the tissue product can also achieve a higher bulk value (defined as caliper/basis weight) than typically possible for calendered facial tissue products.

Referring back to FIG. 3, when fed around the shear-inducing roll 64, base web 38 should generally have a low moisture content. For example, the base web 38 should have a moisture content of less than about 10% by weight, particularly less than about 5% by weight. Because the base web can be fed around the shear-inducing roll while it is essentially dry, when and where this processing step is carried out can be varied as desired. For example, the shear inducing process can be carried out immediately subsequent to web formation, such that the shear inducing rolls are located between the creping blade and the take-up reel. Alternatively, the web can be subject to the shear inducing processes of the present invention during converting operations at some point after the original tissue formation and take up operations.

As shown in FIG. 3, the shear-inducing roll 64 can be a rotating roll having a relatively small diameter. In other embodiments, however, the shear-inducing roll can be a stationary roll. The effective diameter of the shear-inducing roll, for most applications, should be less than about 10 inches, particularly less than about 7 inches, and more particularly from about 2 inches to about six inches.

The amount that conveyors 60 and 62 are wrapped around the shear-inducing roll 64 can vary depending upon the particular application and the amount of shear that is desired to be exerted on the web. For most applications, however, the conveyors should be wrapped around the shear-inducing roll in an amount from about 30° to about 270°, particularly from about 50° to about 200°, and more particularly from about 80° to about 180°. In the embodiment illustrated in FIG. 3, the amount of wrap placed around the shear-inducing roll can be adjusted by adjusting the position of either the shear-inducing roll 64 or the support rolls 66 and 68. For instance, by moving the shear-inducing roll 64 down closer to the support rolls 66 and 68, the conveyors will wrap around the shear-inducing roll 64 to a lesser extent.

As described above, in addition to the amount of wrap that is placed around the shear-inducing roll, the amount of tension placed upon the conveyors 60 and 62 can also have an impact on the amount of shear and compression that is exerted on the base web 38. The amount of tension placed upon the conveyors will depend upon the particular application. For most applications, however, the conveyors 60 and 62 should be placed under tension in an amount from about 5 pounds per linear inch to about 90 pounds per linear inch, particularly from about 10 pounds per linear inch to about 50 pounds per linear inch, and more particularly from about 30 pounds per linear inch to about 40 pounds per linear inch.

When the conveyors 60 and 62 are wrapped around the shear-inducing roll 64 under a sufficient amount of tension, a surface speed differential develops between the two surfaces of the web that creates the shear forces. For most applications, the speed differential should be from about 0.5% to about 5%, and particularly from about 1% to about 3% with conveyor on the outside moving faster than the conveyor contacting the roll.

During this process, the tactile properties of the base web can be greatly enhanced, without seriously affecting the strength of the web. In some applications, additional softness can be imparted to the web by application of a softening agent as the web is being fed around the shear inducing roll. For example, certain softening agents, such as, for example, a polysiloxane chemical additive can be applied to the web in order to impart additional softness to the product. In accordance with the present invention, the softening agent can be applied to one or both of the forming fabrics which overlie the web during the process. Application of the softening agent to the forming fabrics can be by any suitable method. For example, the fabric can be sprayed or brushed with the additive either prior to or after contact with the web. Alternatively, the fabric can be dipped in the softening agent prior to contact with the web. The softening agent can then be transferred to the web from the fabric while the shear inducing process is being carried out.

In a finishing process, it may be desired to impart a light calendering to the product in order to, for example, impart a smoother finish to the product surface. Any calendering would have to be delivered at a light enough pressure, however, such that the unique product properties obtained through the process of the present invention are not subsequently destroyed by the calendering process.

Figure 4:
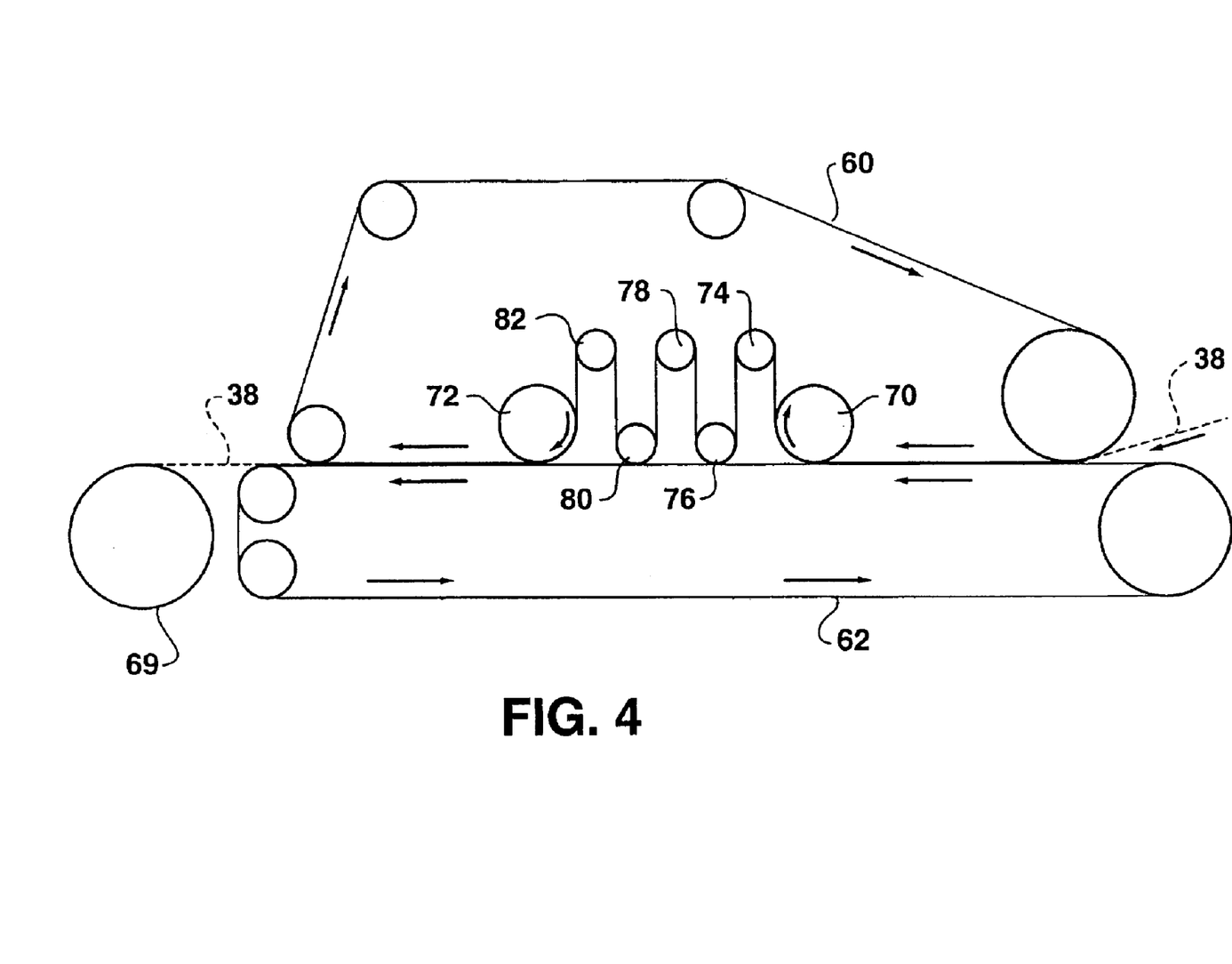
FIG. 4 is a schematic diagram of an alternative embodiment of a process for improving the tactile properties of a formed base web made in accordance with the present invention.

In the embodiment illustrated in FIG. 3, the system includes a single shear-inducing roll 64. In other embodiments, however, more shear-inducing rolls can be used. For instance, in other embodiments, the conveyors can be wrapped around two shear-inducing rolls, three shear-inducing rolls, and even up to ten shear-inducing rolls. Referring to FIG. 4, an alternative embodiment of the present invention is illustrated that includes five shear-inducing rolls.

As shown, the base web 38 is fed between the first conveyor 60 and the second conveyor 62 and is then wrapped around support rolls 70 and 72 and shear-inducing rolls 74, 76, 78, 80, and 82. In general, using more shear-inducing rolls can create more shear that is exerted on the base web. Although the shear-inducing rolls are illustrated as having approximately equal diameters, alternative embodiments may be desired with some or all of the shear-inducing rolls having diameters which are unequal to the others.

When using more than one shear-inducing roll, the total wrap of the conveyors around all of the shear-inducing rolls should be at least 90° for most embodiments. More particularly, especially when using more than two shear-inducing rolls, the total wrap should be greater than 100°, and particularly greater than 120°. The total wrap, however, can increase or decrease depending upon increasing or decreasing the number of shear-inducing rolls respectively.

Figure 5:
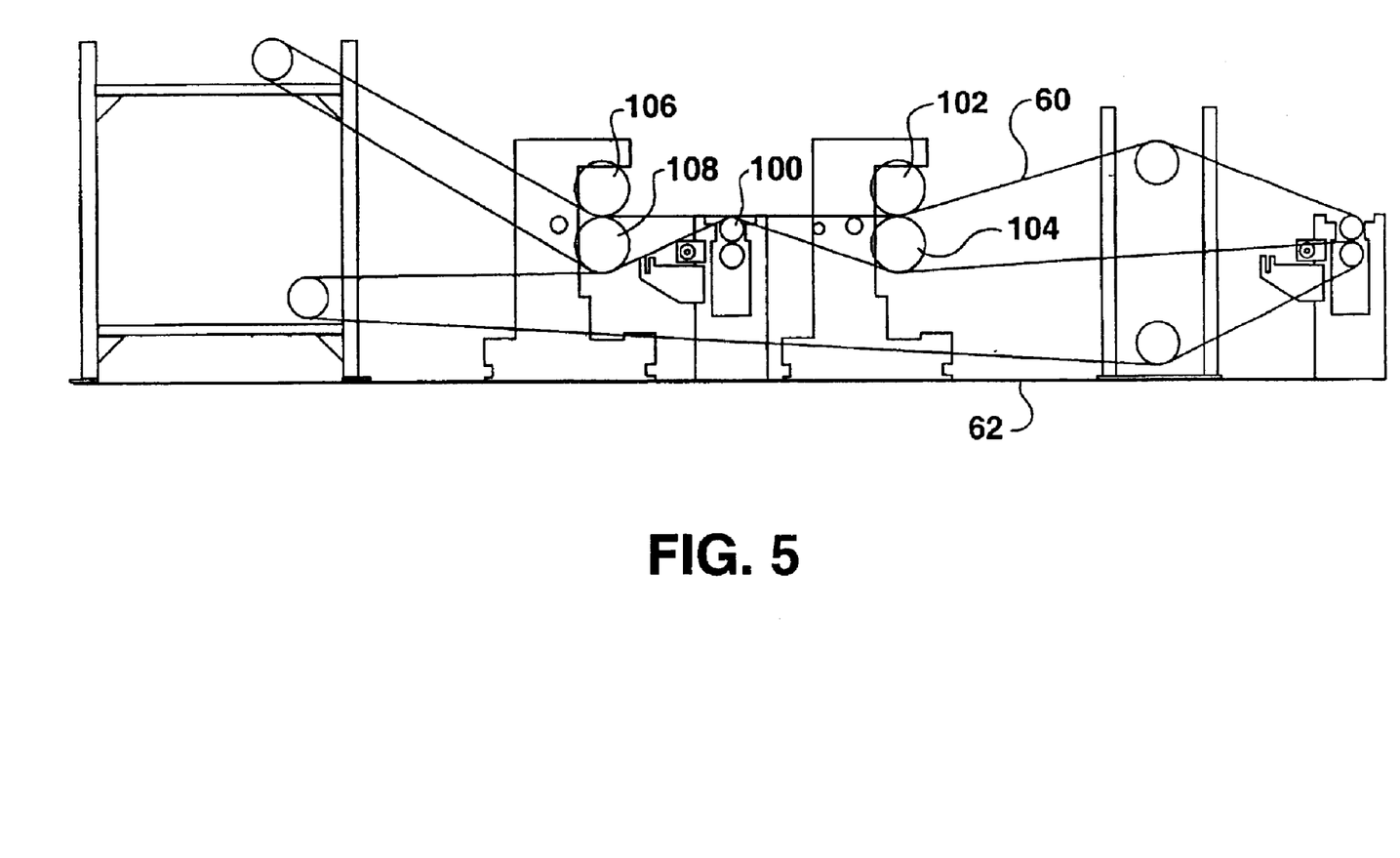
FIG. 5 is a schematic diagram of another alternative embodiment of a process for improving the tactile properties of a formed base web made in accordance with the present invention.
Figure 6:
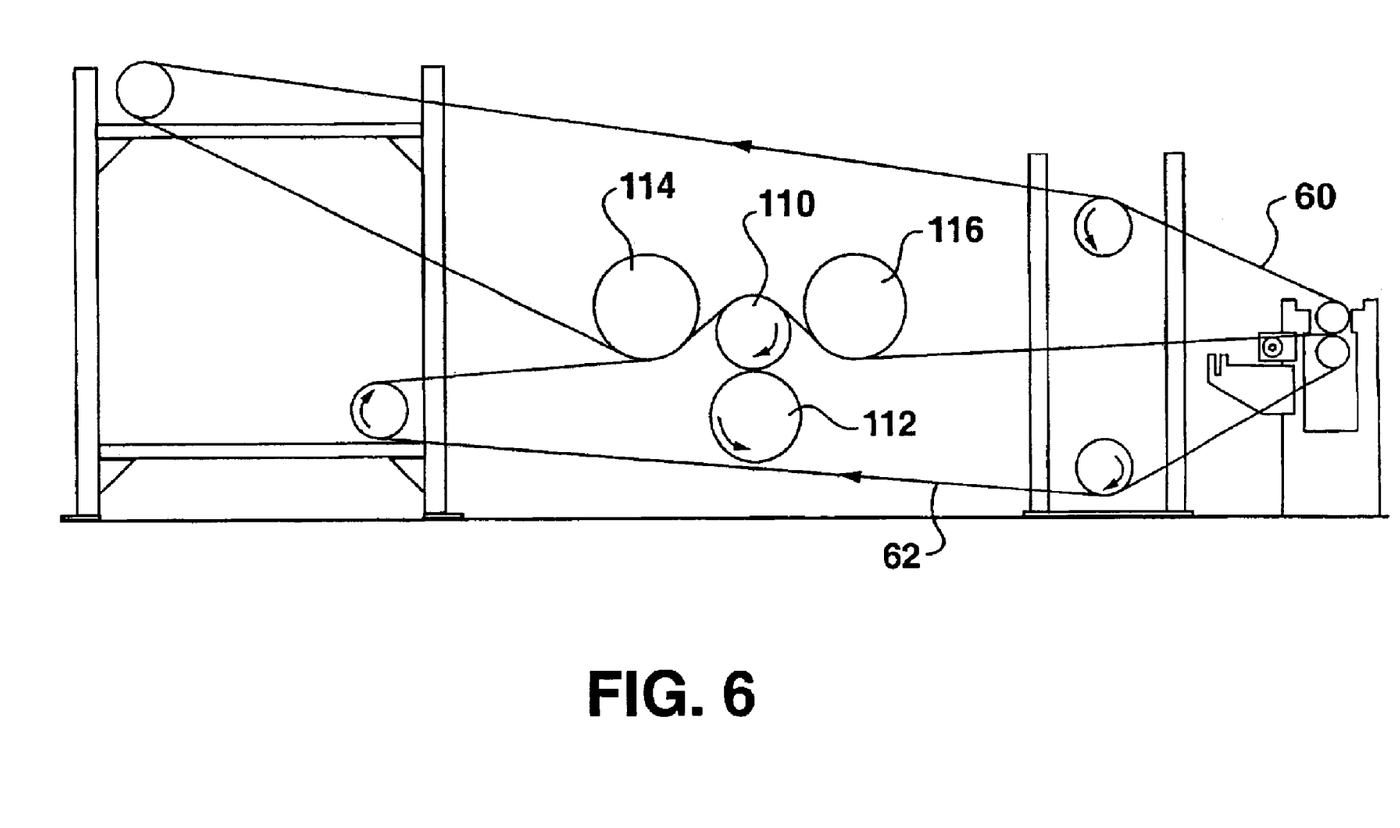
FIG. 6 is a schematic diagram of a further alternative embodiment of a process for improving the tactile properties of a formed base web made in accordance with the present invention.

Further embodiments of systems made in accordance with the present invention are illustrated in FIGS. 5 and 6. The system illustrated in FIG. 5 includes a single shear-inducing roll 100. As shown, conveyors 60 and 62 are guided around the shear-inducing roll 100 by support rolls 102, 104, 106 and 108.

The system illustrated in FIG. 6 also includes a single shear-inducing roll 110. It should be understood, however, that more shear-inducing rolls can be included in any of the systems illustrated. As shown in FIG. 6, shear-inducing roll 110 is supported by a backing roll 112. In order to facilitate the amount of wrap around shear-inducing roll 110, the system further includes support rolls 114 and 116.

As stated above, base webs processed according to the present invention can be made from various materials and fibers. For instance, the base web can be made from pulp fibers, other natural fibers, synthetic fibers, and the like.

For instance, in one embodiment of the present invention, the base web contains pulp fibers either alone or in combination with other types of fibers. The pulp fibers used in forming the web can be, for instance, softwood fibers having an average fiber length of greater than 1 mm and particularly from about 2 to 5 mm based on a length weighted average. Such fibers can include Northern softwood kraft fibers. Secondary fibers obtained from recycled materials may also be used.

In one embodiment, staple fibers (and filaments) can be added to the web to increase the strength, bulk, softness and smoothness of the web. Staple fibers can include, for instance, polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have fiber lengths of 5 mm and greater.

The staple fibers added to the base web can also include bicomponent fibers. Bicomponent fibers are fibers that can contain two materials such as, but not limited to, in a side by side arrangement or in a core and sheath arrangement. In a core and sheath fiber, generally the sheath polymer has a lower melting temperature than the core polymer. For instance, the core polymer, in one embodiment, can be nylon or a polyester, while the sheath polymer can be a polyolefin such as polyethylene or polypropylene. Such commercially available bicomponent fibers include CELBOND fibers marketed by the Hoechst Celanese Company.

The staple fibers used in the base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the Z direction as well as increase web strength properties.

In one embodiment, when forming paper products containing pulp fibers, the staple fibers can be added to the web in an amount from about 5% to about 30% by weight and particularly from about 5% to about 20% by weight.

When the base web of the present invention is not used to make paper products, but instead is incorporated into other products such as diapers, feminine-hygiene products, garments, personal-care products, and various other products, the base web can be made from greater amounts of staple fibers.

Besides pulp fibers and staple fibers, thermomechanical pulp can also be added to the base web. Thermomechanical pulp, as is known to one skilled in the art, refers to pulp that is not cooked during the pulping process to the same extent as conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, the thermomechanical pulp can be added to the base web in an amount from about 10% to about 30% by weight. When using thermomechanical pulp, a wetting agent is also preferably added during formation of the web. The wetting agent can be added in an amount less than about 1% and, in one embodiment, can be a sulphonated glycol.

In some embodiments, it is desirable to limit the amount of inner fiber-to-fiber bond strength. In this regard, the fiber furnish used to form the base web can be treated with a chemical debonding agent. The debonding agent can be added to the fiber slurry during the pulping process or can be added directly into the headbox or can be applied to one or both of the conveyors which overlie the web in the process of the present invention. Suitable debonding agents that may be used in the present invention include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun which is incorporated herein by reference.

In one embodiment, the debonding agent used in the process of the present invention can be an organic quaternary ammonium chloride. In this embodiment, the debonding agent can be added to the fiber slurry in an amount from about 0.1% to about 1% by weight, based on the total weight of fibers present within the slurry.

The base web of the present invention may also have a multi-layer construction. For instance, the web can be made from a stratified fiber furnish having at least three principal layers.

It has been discovered by the present inventors that various unique products can be formed when processing a stratified base web according to the present invention. For example, as described above, the process of the present invention causes web disruption in the area of the web that is weakest. Consequently, one particular embodiment of the present invention is directed to using a stratified base web that contains weak outer layers and a strong center layer. Upon exposure to the shear forces created through the process of the present invention, bonds are broken on the outer surface of the sheet, while the strength of the center layer is maintained. The net effect is a base web having improved softness and stiffness with minimal strength loss.

In an alternative embodiment, a stratified base web can be used that has outer layers having a greater tensile strength than a middle layer. In this embodiment, upon exposure to the shear forces created by the process of the present invention, bonds in the middle layer fail but the integrity of the outer layers is maintained. The resulting sheet simulates, in some respects, the properties of a two-ply sheet.

There are various methods available for creating stratified base webs. For instance, referring to FIG. 1, one embodiment of a device for forming a multi-layered stratified fiber furnish is illustrated. As shown, a three-layered headbox generally 10 may include an upper headbox wall 12 and a lower headbox wall 14. Headbox 10 may further include a first divider 16 and a second divider 18, which separate three fiber stock layers. Each of the fiber layers 24, 20, and 22 comprise a dilute aqueous suspension of fibers.

Figure 1:
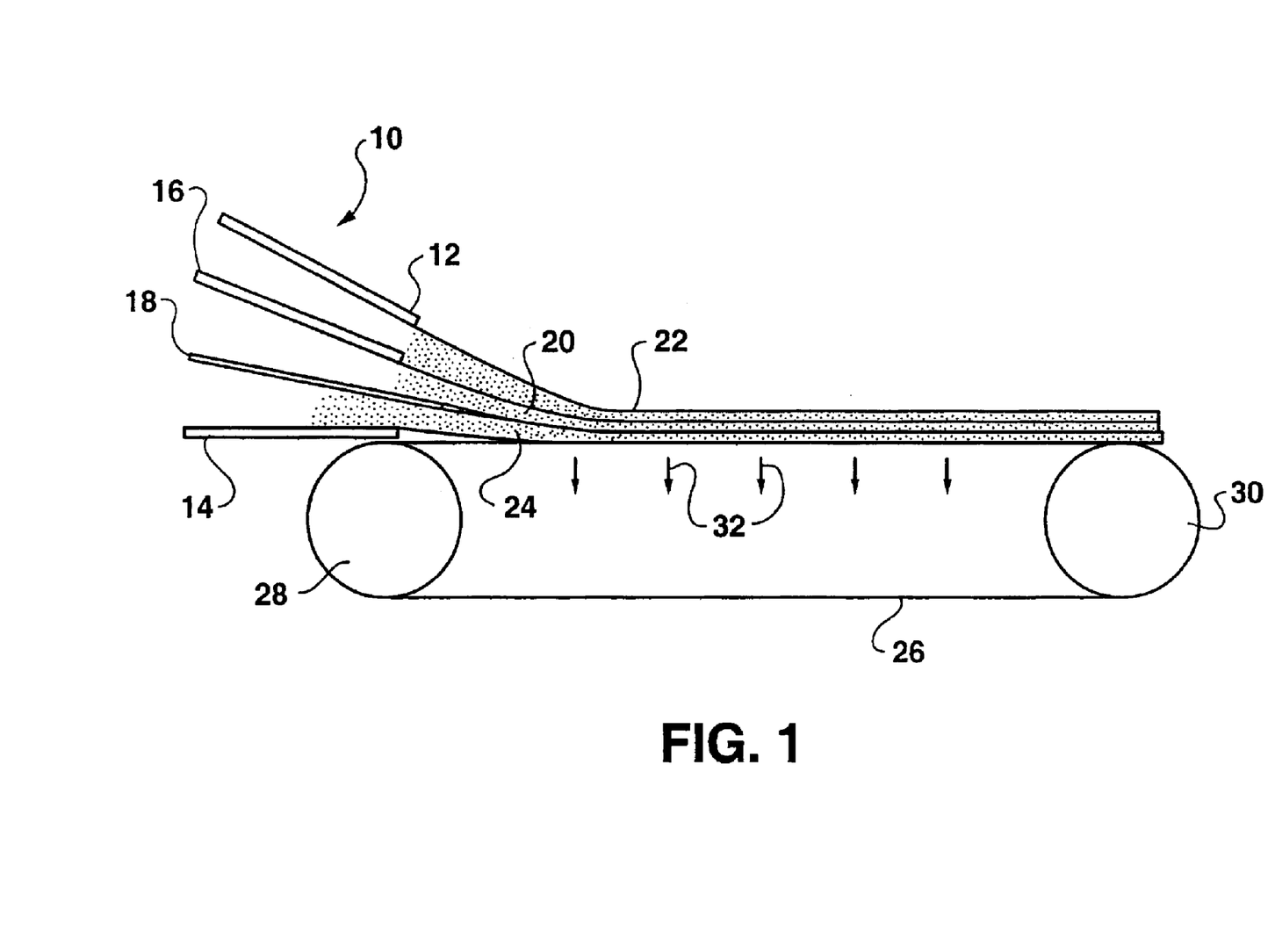
FIG. 1 is a schematic diagram of a fibrous web forming machine illustrating one embodiment for forming a base web having multiple layers in accordance with the present invention.

An endless traveling forming fabric 26, suitably supported and driven by rolls 28 and 30, receives the layered stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

Forming multi-layered webs is also described and disclosed in U.S. Pat. No. 5,129,988 to Farrington, Jr. and in U.S. Pat. No. 5,494,554 to Edwards, et al., which are both incorporated herein by reference.

In forming stratified base webs, various methods and techniques are available for creating layers that have different tensile strengths. For example, debonding agents can be used as described above in order to alter the strength of a particular layer.

Alternatively, different fiber furnishes can be used for each layer in order to create a layer with desired characteristics. For example, in one embodiment, softwood fibers can be incorporated into a layer for providing tensile strength, while hardwood fibers can be incorporated into an adjacent layer for creating a weaker tensile strength layer.

More particularly, it is known that layers containing hardwood fibers typically have a lower tensile strength than layers containing softwood fibers. Hardwood fibers have a relatively short fiber length. For instance, hardwood fibers can have a length of less than about 2 millimeters and particularly less than about 1.5 millimeters.

In one embodiment, the hardwood fibers incorporated into a layer of the base web include eucalyptus fibers. Eucalyptus fibers typically have a length of from about 0.8 millimeters to about 1.2 millimeters. When added to the web, eucalyptus fibers increase the softness, enhance the brightness, increase the opacity, and increase the wicking ability of the web.

Besides eucalyptus fibers, other hardwood fibers may also be incorporated into the base web of the present invention. Such fibers include, for instance, maple fibers, birch fibers and possibly recycled hardwood fibers.

In general, the above-described hardwood fibers can be present in the base web in any suitable amount. For example, the fibers can comprise from about 5% to about 100% by weight of one layer of the web.

The hardwood fibers can be present within the lower tensile strength layer of the web either alone or in combination with other fibers, such as other cellulosic fibers. For instance, the hardwood fibers can be combined with softwood fibers, with superabsorbent materials, and with thermomechanical pulp.

As described above, stronger tensile strength layers can be formed using softwood fibers, especially when adjacent weaker tensile strength layers are made from hardwood fibers. The softwood fibers can be present alone or in combination with other fibers. For instance, in some embodiments, staple fibers, such as synthetic fibers, can be combined with the softwood fibers.

The weight of each layer of a stratified base web in relation to the total weight of the web is generally not critical. In most embodiments, however, the weight of each outer layer will be from about 15% to about 40% of the total weight of the web, and particularly from about 25% to about 35% of the weight of the web.

The basis weight of base webs made according to the present invention can vary depending upon the particular application. In general, for most applications, the basis weight can be from about 5 pounds per 2,880 square feet (ream) (8.5 gsm) to about 80 pounds per ream (136 gsm), and particularly from about 6 pounds per ream (10.2 gsm) to about 30 pounds per ream (51 gsm). For example, a creped web product of the present invention can have a basis weight of less than about 35 gsm. In one embodiment, the present invention can be used to construct a single ply bath tissue having a basis weight of from about 5 gsm to about 40 gsm. Some other uses of the base webs include use as a wiping product, as a napkin, as a medical pad, as an absorbent layer in a laminate product, as a placemat, as a drop cloth, as a cover material, as a facial tissue, or for any product that requires liquid absorbency.

The present invention may be better understood with reference to the following examples.

EXAMPLE 1

In this example, base sheets were produced according to conventional wet-pressed tissue manufacture methods. One of the base sheets produced was then fed between two fabrics, and guided around a series of three shear inducing rolls. The shear inducing rolls all had a roll diameter of 2.5 inches. The tissue was fed around the shear inducing roll between the two fabrics at a rate of 500 feet/minute. Neither of the base sheets were calendered.

Strength was determined using a geometric mean tensile strength test (GMT). In particular, the tensile strength of samples was determined in the machine direction and in the cross machine direction. The size of the samples tested were 3 inches in width unless indicated to the contrary. During the test, each end of a sample was placed in an opposing clamp. The clamps held the material in the same plane and moved apart at a ten inch per minute rate of extension. The clamps moved apart until breakage occurred in order to measure the tensile strength of the sample. The geometric mean tensile strength is then calculated by taking the square root of the machine-direction tensile strength of the sample multiplied by the cross-direction tensile strength of the sample.

Tensile strength tests can be performed, for instance, on the Sintech 2 tester, available from the Sintech Corporation of Cary, N.C., the Instron Model TM available from the Instron Corporation of Canton, Mass., a Thwing-Albert Model INTELLECT II available from the Thwing-Albert Instrument Company of Philadelphia, Pa., or SYNERGY 100 available from MTS Systems, Corp. located in Eden Prairie, Minn. Results are reported in grams or in grams per inch width of sample.

Caliper of the web was determined by use of an EMVECO 200A Tissue Caliper Tester. Throughout the experimental procedures, caliper was measured at a load of about 2.00 kPa over an area of about 2500 mm$^2$.

Geometric mean modulus is the square root of the product of the modulus in the machine direction (in kilograms) and the modulus in the cross direction (in kilograms) of the web.

Fuzziness, Grittiness, and Stiffness values were obtained through a Sensory Profile Panel testing method. A group of 12 trained panelists were given a series of tissue prototypes, one sample at a time. Samples were in the form of two continuous sheets for each sample. For each sample, the panelists rate the tissue for fuzziness, grittiness and stiffness on a scale of 1 (low) to 16 (high) in a sequential, monadic fashion. Results are reported as an average of panel rankings.

Resulting products are compared below in Table 1.

TABLE 1

|  | Standard Basesheet | Basesheet after shear inducing processing |
| --- | --- | --- |
| Basis weight (gsm) | 32.3 | 29.7 |
| Caliper (microns) | 310 | 287 |
| Geometric Mean Tensile Strength (grams/inch) | 350 | 291 |
| Bulk (cc/gram) | 9.61 | 9.67 |
| Geometric Mean Modulus (kg) | 9.85 | 7.39 |
| Fuzzy | 6.45 | 7.43 |
| Gritty | 2.34 | 2.15 |
| Stiffness | 4.79 | 3.94 |

As can be seen, after subjection to the shear inducing process of the present invention, the tissue product exhibits significant softening with less densification than would be expected to occur during steel on steel calendering.

EXAMPLE 2

Base sheets were produced according to conventional wet-pressed tissue manufacture methods. After manufacture, a base sheet was fed between two fabrics, and then guided around a shear inducing roll. An air atomized spray application of Dow Corning 2-1938 silicone emulsion was sprayed onto the lower fabric of the fabric/basesheet "sandwich" during the shear inducing process. A sample of the resultant tissue sheet was analyzed for the presence of silicone using x-ray fluorescence methods. The net x-ray fluorescence silicone count was 3213 on the tissue sample. For comparison, a standard tissue product having approximately 0.2% to 0.3% silicone addition can have an x-ray fluorescence silicone count of about 2142. Therefore, transfer of the softening agent to the tissue product via the fabrics in the disclosed shear inducing process is clearly feasible.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A paper product comprising:
   a creped nonwoven base web comprising a first side and a second side, said base web containing pulp fibers;
   a crepe pattern formed on said base web; and
   a first fabric-imprinted pattern, wherein said first fabric-imprinted pattern is superimposed upon said crepe pattern on said first side of said base web, said first fabric-imprinted pattern comprising high density troughs that extend in a machine direction, wherein said high density troughs are separated by about 3 mm to about 4 mm.

2. A paper product as defined in claim 1, wherein said base web has a second fabric-imprinted pattern superimposed upon said crepe pattern on said second side of said base web, said second fabric-imprinted pattern comprising high density troughs.

3. A paper product as defined in claim 1, wherein said base web has a basis weight of greater than about 20 gsm.

4. A paper product as defined in claim 1, wherein said paper product comprises a single-ply product.

5. A paper product as defined in claim 1, wherein said paper product comprises a stratified web.

6. A paper product as defined in claim 1, wherein said base web has a geometric mean tensile strength of greater than about 200 g/in.

7. A paper product as defined in claim 1, wherein said base web has a geometric mean tensile strength of greater than about 250 g/in.

8. A paper product as defined in claim 1, wherein said base web has a bulk greater than about 7.5 cc/gram.

9. A paper product as defined in claim 1, wherein said base web has a bulk greater than about 8.5 cc/gram.

10. A paper product as defined in claim 1, wherein said base web has a caliper greater than about 250 microns.

11. A paper product as defined in claim 1, wherein said base web has a caliper greater than about 275 microns.

12. A soft tissue comprising:
    a creped nonwoven base web comprising a first side and a second side, said base web containing pulp fibers;
    a crepe pattern formed on said base web;
    a first fabric-imprinted pattern, wherein said first fabric-imprinted pattern is superimposed upon said crepe pattern on said first side of said base web, said first fabric-imprinted pattern comprising high density troughs that extend in either a machine direction or a diagonal direction, wherein said high density troughs are separated by about 3 mm to about 4 mm in the machine direction, and wherein said high density troughs are separated by about 2 mm to about 3 mm in the diagonal direction; and
    wherein said soft tissue has a caliper greater than about 250 microns.

13. A soft tissue as defined in claim 12, wherein said base web has a second fabric-imprinted pattern superimposed upon said crepe pattern on said second side of said base web, said second fabric-imprinted pattern comprising high density troughs.

14. A soft tissue as defined in claim 12, wherein said base web has a basis weight between about 5 gsm and about 40 gsm.

15. A soft tissue as defined in claim 12, wherein said tissue comprises a single-ply tissue.

16. A soft tissue as defined in claim 12, wherein said base web comprises a stratified web.

17. A soft tissue as defined in claim 12, wherein said tissue has a geometric mean tensile strength of greater than about 200 g/in.

18. A soft tissue as defined in claim 12, wherein said tissue has a geometric mean tensile strength of greater than about 250 g/in.

19. A soft tissue as defined in claim 12, wherein said tissue has a bulk greater than about 7.5 cc/gram.

20. A soft tissue as defined in claim 12, wherein said tissue has a bulk greater than about 8.5 cc/gram.

21. A soft tissue as defined in claim 12, wherein said tissue has a caliper greater than about 275 microns.

22. A paper product comprising:
    a creped nonwoven base web comprising a first side and a second side, said base web containing pulp fibers;
    a crepe pattern formed on said base web; and
    a first fabric-imprinted pattern, wherein said first fabric-imprinted pattern is superimposed upon said crepe pattern on said first side of said base web, said first fabric-imprinted pattern comprising high density troughs that extend in a machine direction and in a diagonal direction; and
    wherein said base web has a bulk greater than about 8.5 cc/gram, a caliper greater than about 250 microns, and a geometric mean tensile strength of greater than about 250 g/in.

* * * * *